United States Patent [19]

Ali

[11] Patent Number: 4,554,819

[45] Date of Patent: * Nov. 26, 1985

[54] METHOD OF AND APPARATUS FOR MEASURING IN SITU, THE SUBSURFACE BEARING STRENGTH, THE SKIN FRICTION, AND OTHER SUBSURFACE CHARACTERISTICS OF THE SOIL

[76] Inventor: Muhammad A. Ali, 10507 Odessa Dr., Sugar Land, Tex. 77478

[*] Notice: The portion of the term of this patent subsequent to Aug. 30, 2000 has been disclaimed.

[21] Appl. No.: 536,679

[22] Filed: Sep. 28, 1983

[51] Int. Cl.$^4$ .................. G01N 3/42; G01N 19/02
[52] U.S. Cl. ........................................ 73/9; 73/84
[58] Field of Search .................. 73/9, 84, 864.44

[56] References Cited

U.S. PATENT DOCUMENTS

| | | | |
|---|---|---|---|
| 3,042,124 | 7/1962 | Andersson | 73/864.44 |
| 3,481,188 | 12/1969 | Mori | 73/84 |
| 3,958,646 | 5/1976 | Pellissier | 173/46 |
| 3,999,424 | 12/1976 | Pellissier | 73/84 |
| 4,400,970 | 8/1983 | Ali | 73/9 |

Primary Examiner—S. Clement Swisher
Attorney, Agent, or Firm—Vaden, Eickenroht, Thompson & Jamison

[57] ABSTRACT

The invention disclosed includes a method of and apparatus for measuring the subsurface bearing strength of soil and the frictional resistance of the soil to movement of a pile through the soil. A probe is used for this purpose that includes two relatively movable members, an inner plunger with a flat face, and an outer tubular member. By measuring the forces imposed by the soil at different locations on the probe as the relatively movable members of the probe are moved through the soil the bearing capacity and the skin friction of the soil can be calculated.

10 Claims, 16 Drawing Figures

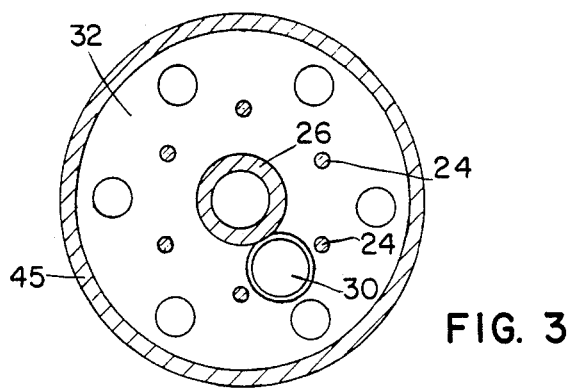
FIG. 3
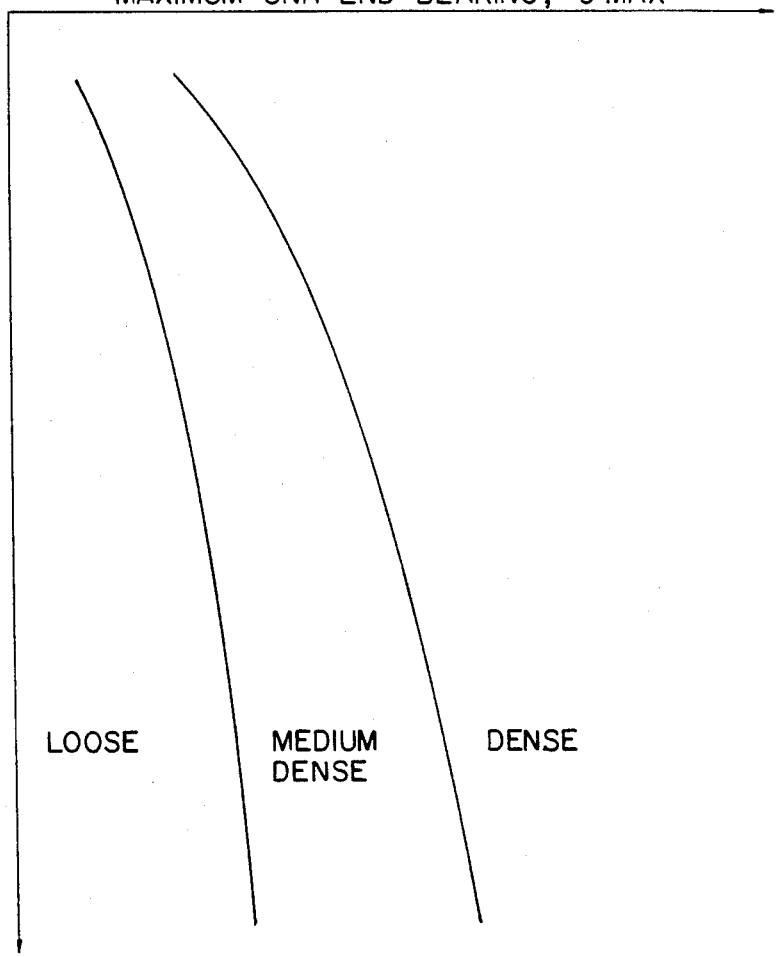
FIG. 7 — MAXIMUM UNIT END BEARING VERSUS DEPTH CURVES FOR DETERMINATION OF SOIL DENSITY FIG. 8 FRICTION RATIO VERSUS ANGLE OF INTERNAL FRICTION CURVES
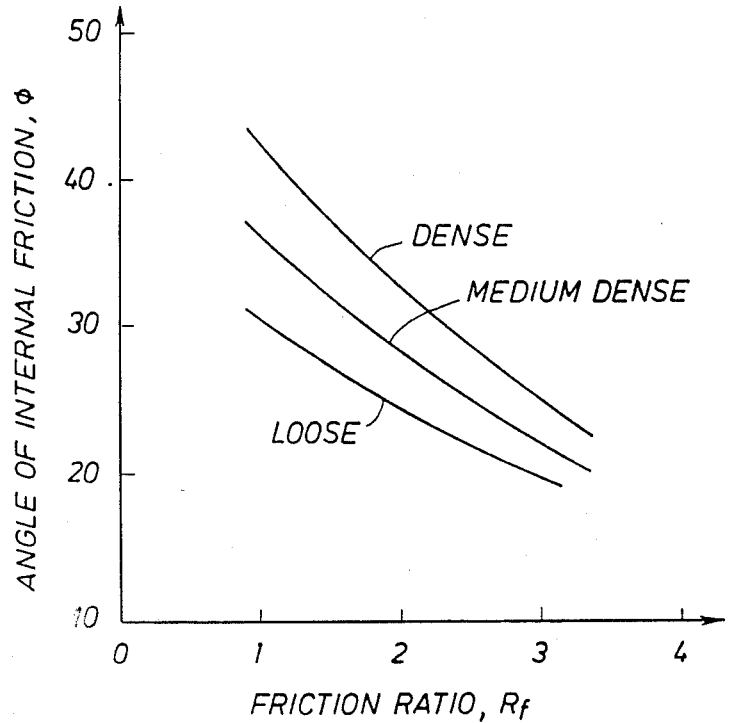
FIG. 9 MAXIMUM UNIT END BEARING VERSUS EFFECTIVE VERTICAL STRESS CURVES
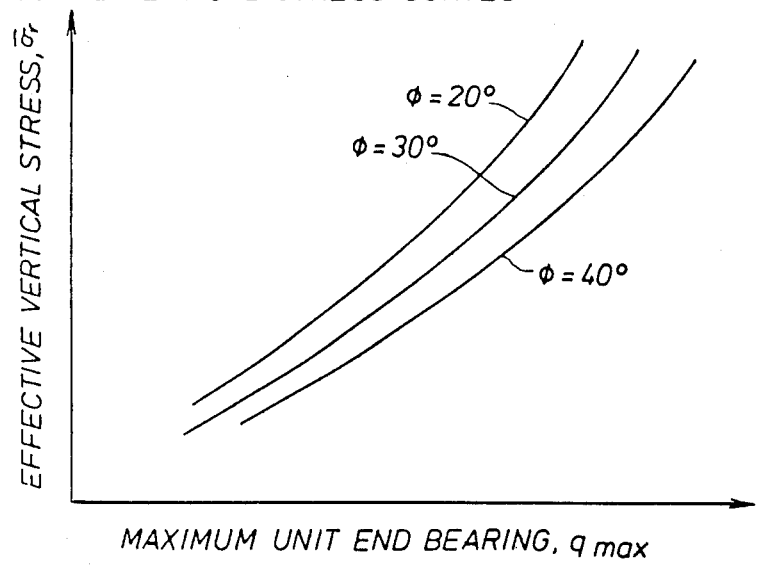

METHOD OF AND APPARATUS FOR MEASURING IN SITU, THE SUBSURFACE BEARING STRENGTH, THE SKIN FRICTION, AND OTHER SUBSURFACE CHARACTERISTICS OF THE SOIL

This invention relates generally to soil testing to obtain information useful in the design of a foundation so that it and the structure to be built on the foundation will be adequately supported by the soil. In one aspect, the invention relates to a method of and apparatus for measuring in situ such sub-soil characteristics as its subsurface bearing strength and the frictional resistance of the soil to movement of a pile through the soil, commonly called skin friction. In another aspect, this invention relates a method of and apparatus for measuring the change in skin friction due to cyclic movement of a pile in the soil. In yet another aspect, this invention relates to a method and apparatus for measuring the resistance of the soil to an upward movement of a pile located in the soil.

This patent application is related to the information described U.S. Pat No. 4,400,970.

The foundation for any structure should be designed with adequate knowledge of the subsurface conditions of the soil that is going to support the foundation and the structure to be placed on the foundation. This information is presently obtained by field testing and by laboratory testing of soil samples obtained by soil borings. The soil samples, however, are disturbed when they are removed from the ground and transported to a laboratory. Further, field conditions or in situ conditions of the soil cannot always be simulated in the laboratory.

Therefore, usually, some in situ tests are also conducted. These in situ probes measure some soil properties, such as shear strength, permeability, bearing capacity, and so forth, which are mainly used for strategraphic correlations. Information thus obtained, however, is not considered adequate for foundation design work; more information is desired. In particular, since the skin friction and the end bearing values of a pile are functions of pile movement, it is desirable that the variation of the soil resistance at the pile tip due to movement of the tip and the changes in skin friction due to pile movement be known by the foundation designer. At the present time, this information is obtained empirically based upon information obtained from the soil samples and test data and includes a substantial amount of personal judgment on the part of the person interpreting the information.

Therefore, it is an object of this invention to provide a method of and apparatus for obtaining information about the subsurface characteristics of a soil in situ from which the variation of resistance, q, at the pile tip due to tip movement, z, (q-z curve) can be obtained.

It is a further object of this invention to provide a method of and apparatus for obtaining accurate measurements of subsurface soil conditions in situ from which changes in compressive skin friction, f, due to pile movement, z (f-z curve) can be obtained.

It is a further object of this invention to provide a method of and apparatus for obtaining subsurface soil information in situ from which an f-z curve for tensile skin friction can be determined.

It is a further object of this invention to provide a method of and apparatus for obtaining accurate measurements of the degredation of the skin friction offered by the soil due to cyclic loading of a pile located in the soil and other soil characteristics for design and stratigraphic correlations.

These and other objects, advantages, and features of this invention will be apparent to those skilled in the art from consideration of this specification including the attached drawings and appended claims.

IN THE DRAWINGS

FIG. 1 is a view, partly in section and partly in elevation, of the apparatus of this invention extending through a hollow core bit to engage the bottom of a well bore preparatory to testing subsurface characteristics of the soil in accordance with the method of this invention;

FIGS. 2A, 2B, and 2C are vertical sectional views taken through the preferred embodiment of the apparatus of this invention;

FIG. 3 is a sectional view taken along line 3—3 of FIG. 2B;

FIG. 7 is a family of curves showing the relationship of soil density to maximum unit end bearing and depth;

FIG. 8 is a family of curves showing the relationship of friction ratio to the angle of internal friction for different soil densities; and FIG. 9 is a graph of the relationship between maximum unit end bearing and effective vertical stress for different angles of internal friction.

The apparatus of this invention can be used to measure sub-soil conditions by positioning the apparatus on the surface of the soil, anchoring the apparatus against upward movement, and causing the various elements of the apparatus to penetrate into the soil in the manner described below. Usually, however, a well bore will be drilled into the soil a preselected distance and the apparatus will operate through the drill pipe to measure the soil conditions directly below the bottom of the well bore.

Figure 1:
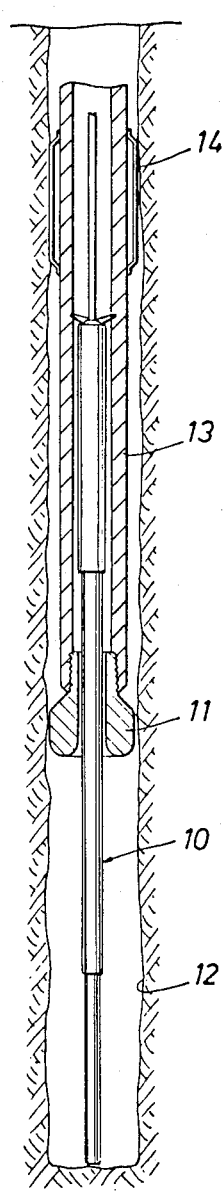

This is the arrangement shown in FIG. 1, where the apparatus, indicated generally by the number 10, extends through core bit 11 to engage the bottom of well bore 12. The core bit is attached to drill string 13, which in turn is supported by a core drilling rig located at the surface of the ground or on a ship or barge, if the soil being tested is below a body of water. Before the soil testing begins, the drilling rig raises core bit 11 from the bottom of the well bore. The apparatus of this invention is then lowered through the drill pipe into engagement with the bottom of the well bore as shown in FIG. 1. Stabilizer 14, or if desired an inflatable packer, is used to hold the drill pipe against lateral movement, which could disturb the operation of the apparatus and cause erroneous measurements to be made.

Further, if the drill string is being supported from a floating vessel, unless the water is extremely smooth, a heave compensator of some type should be used to isolate the drill pipe from the vertical movement of the vessel due to waves.

Figure 2A:
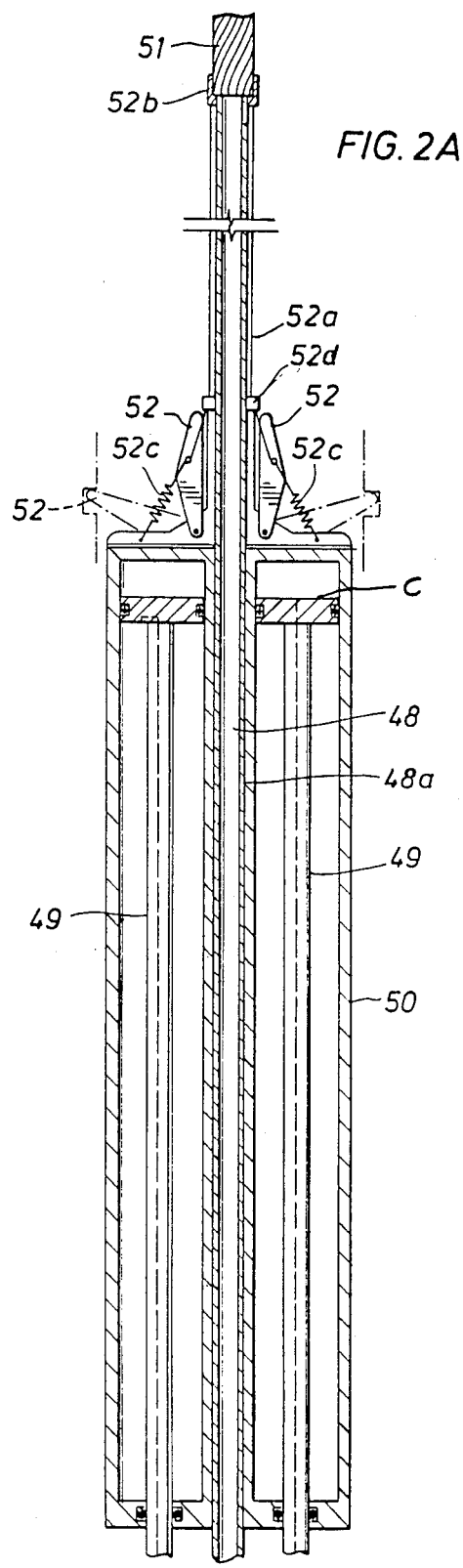
Figure 2B:
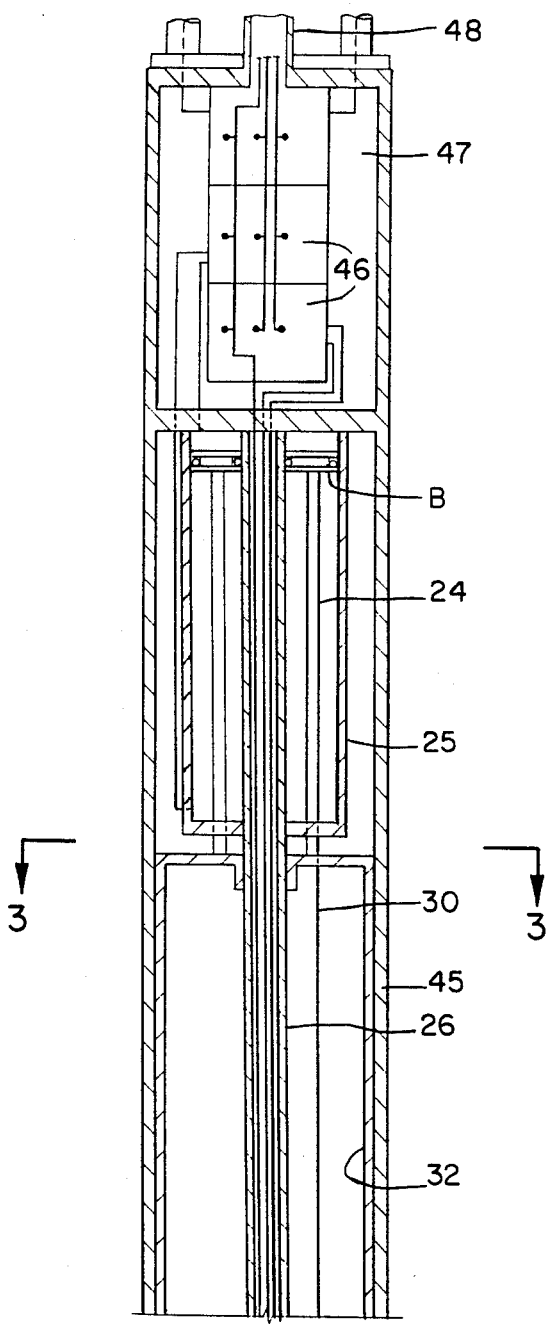
Figure 2C:
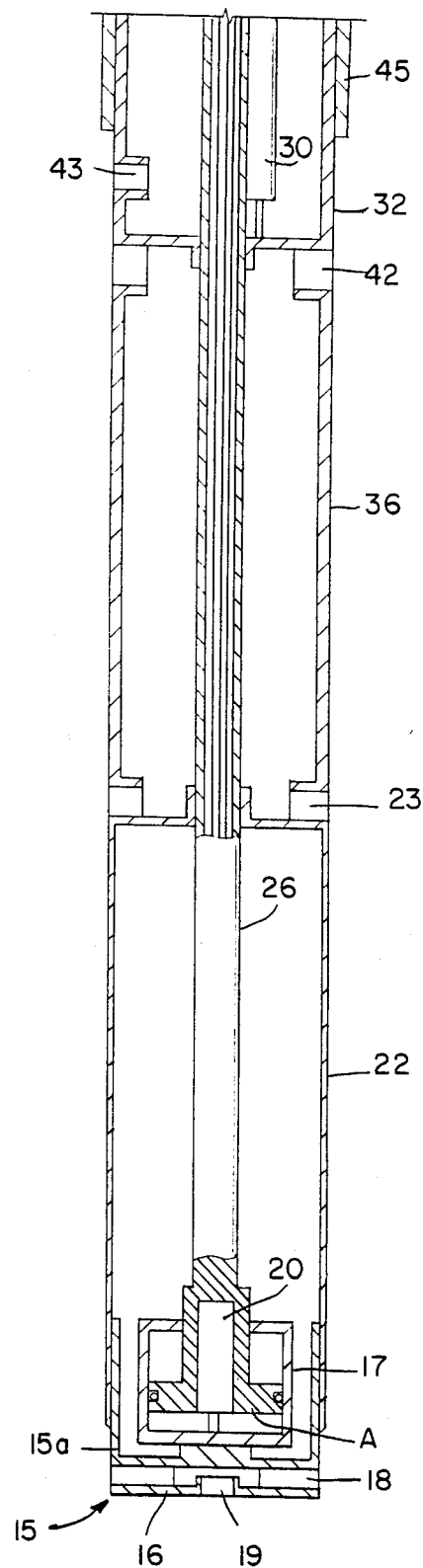

Referring to FIG. 2C, the apparatus will be described from the bottom up. Generally, the apparatus is designed to provide two basic components, one simulating the end or tip of a pile and the other simulating the side of a pile.

In the embodiment shown, the apparatus includes three pistons located in three cylinders, each of which moves various parts of the apparatus. All of the pistons are double-acting and in this embodiment they are powered by hydraulic fluid.

Located at the bottom of the apparatus is plunger 15 comprising cylindrical, cup-shaped element 15a, load cell 18, which is connected to the bottom of cup-shaped element 15a, and disc-shaped member 16, which is attached to the bottom side of load cell 18. The plunger simulates the tip of a pile. It is attached to cylinder 17 for movement with the cylinder. Piston A is located inside cylinder 17 and connected to the lower end of rod 26. Hydraulic pressure below piston A will move the plunger downwardly relative to the piston. Hydraulic pressure above piston A will move the plunger upwardly relative to the piston. Pressure transducer 19 is mounted in the center of disc-shaped member 16 to measure pore water pressure below the plunger. The distance the plunger moves relative to piston A is measured by displacement transducer, (LVDT) 20.

The plunger is located in the open end of elongated cylindrical sample tube 22. The upper end of the sample tube is connected to load cell 23, which in turn is connected to the bottom of friction sleeve 36. The sample tube 22 and the friction sleeve 36 have equal outside diameters. The upper end of the friction sleeve is connected to load cell 42. Load cell 42 is attached to the bottom of cylinder 32, which is supported by a plurality of rods 24. The rods are connected to annular piston B, as shown in FIG. 2B. Piston B is located in annular cylinder 25, which surrounds and is connected to rod 26.

As shown in FIG. 3, displacement transducer (LVDT 30) is located alongside rod 26, and connected between the bottom of cylinder 25 and the lower end of cylinder 32 to measure the movement of piston B relative to cylinder 25. Pressure transducer 43 is mounted in the outside wall of cylinder 32 to measure the pore pressure of the soil adjacent the Friction sleeve. For clarity, the electrical conductors serving the load cells, the solenoid valves, and the displacement and pressure transducers have not been shown.

To summarize the apparatus at this point, piston A and cylinder 17 combine to move plunger 15 relative to sample tube 22. Piston B moves sample tube 22 and friction sleeve 36 relative to the plunger.

This assembly extends into and is supported by tubular housing 45. A plurality of solenoid operated valves 46 are positioned in chamber 47 in the upper end of housing 45. The valves are controlled from the surface to direct hydraulic fluid to the cylinders to move the pistons to produce the relative movements of the plunger and the sample tube and friction sleeve described below to obtain the desired measurements. Hydraulic fluid under pressure is supplied from the surface through flexible conduit 48 located inside tubular conduit 48a (FIG. 2A). The electrical conductors required to operate the valves and transmit the measurements of the load cells and the displacement and pressure transducers to the surface are also located in conduit 48.

Housing 45 is connected to piston C, shown in FIG. 2A, by a plurality of piston rods 49 that extend through the lower end of cylinder 50 in which piston C is located. Cylinder 50 can slide up and down on relatively rigid conduit 48a, which is attached at its upper end to support cable 51 by collar 52b. Support cable 51 also provides a protective sheath for conduit 48 through which the electrical conductors and hydraulic or pneumatic conduits extend from the surface to the apparatus.

Located at the upper end of cylinder 50 are a plurality of spring loaded dogs 52. When piston C is in its upper position, flexible lines 52a, each of which has one end connected to upper end 52b of conduit 48a and the other end to one of the dogs, will hold the dogs in the position shown. When the apparatus is resting on the bottom of a well bore, pressure applied to piston C will move the cylinder upwardly. This creates sufficient slack in lines 52a to allow the dogs to be pivoted outwardly by springs 52c into position to engage a groove (not shown) in the drill string to limit the upward movement of the cylinder. Lines 52a slide through guide holes provided in collar 52d.

In operation, the reading of load cell 18 is first adjusted to zero. The apparatus is then lowered through the drill string until its lower end is in engagement with the bottom of the well bore. Air or some other gas is supplied from the surface to maintain the pressure inside the apparatus approximately equal to outside pressure. Before insertion of the probe into the soil, the readings of load cells 23 and 42 are adjusted to zero. Hydraulic pressure is now supplied above piston C to move the lower end of the apparatus, latches or dogs 52 are released as described above to limit the upward movement of the apparatus. As the upward movement is thus prevented, the lower end of the apparatus including plunger 15, sample tube 22, and friction sleeve 36 is forced into the soil below the bottom of the well bore until pressure transducer 43 is below the lower end of the well bore.

As the apparatus is pushed into the soil for making in situ measurements, the soil resists such penetration and therefore becomes stressed. Before making any in situ measurements it is necessary to unload the soil by removing any end bearing and skin friction stresses that have been imposed on the soil. To unload the soil from end bearing stresses, a knowledge of effective vertical stress $\sigma_v$ is needed. There are a number of ways to estimate $\sigma_v$. It is preferred, however, that $\sigma_v$ be estimated by the following procedure.

To unload a soil from end bearing stresses in cohesive material such as clay, the plunger is slowly pulled upwardly after insertion to the desired level. This is done by operating piston A. Whatever pore pressure was generated in the soil below the plunger during insertion starts decreasing during this upward movement. When the pore pressure measured by pressure transducer 19 becomes equal to the hydrostatic pressure at that level, the upward movement of the probe is stopped. The pressure, P, acting against the lower surface of the plunger is now equal to the total vertical stress in the soil at this level and therefore it is considered that the soil has been unloaded from end bearing stress. If, however, $\sigma_v$ is first estimated by some method, then the soil can be unloaded from end bearing by slowly raising the plunger by operating piston A till the reading of load cell 18 is given by Equation 4. After unloading operation, the pressure, P, and the upward movement $u_l$ needed to obtain P are recorded.

In granular material, such as sand, the unit end bearing is mainly dependent on the angle of internal friction and the effective vertical stress. Therefore, a family of curves can be generated relating unit end bearing with the angle of internal friction and effective vertical stress. During insertion of the probe, the maximum end bearing stress $q_{max}$ can be calculated using Equation 1 as follows:

$$q_{max} = \frac{LC_{18max}}{A_{pe}} - h\gamma_w \qquad (1)$$

where, $A_{pe}$ = end area of plunger;
$LC_{18max}$ = maximum reading of load cell 18;
h = depth below free water surface; and
$\gamma_w$ = unit weight of water.

Using $q_{max}$, the soil consistency, loose, medium, or dense, can be assessed from FIG. 7.

It is well known that when a pile is forced into the ground the soil stressed by the pile tip is shaped like a bulb. The bulb of stressed soil extends some distance up the side of the pile and affects skin friction. When the apparatus is pushed in the soil for making in situ measurements, the skin friction is affected by such stress bulb. The maximum unit skin friction that is affected by the end bearing stress bulb is called $f_{a\ max}$.

The value of $f_{a\ max}$ can be obtained from Eq. 2.

$$f_{a\ max} = \frac{1}{\pi D_2 l_f}(LC_{42max} - LC_{23max}) \qquad (2)$$

where, $D_2$ = outer diameter of friction sleeve;
$LC_{23}$, $LC_{24}$ = maximum readings of load cells 23 and 42 during insertion of the probe; and
$l_f$ = length of friction sleeve.

The value of the friction ratio, $R_f$ of the soil is calculated as follows:

$$R_f\% = \frac{f_{a\ max}}{q_{max}} \times 100 \qquad (3)$$

With the friction ratio and soil consistency thus known, the angle of internal friction, $\phi$, can be obtained from FIG. 8. The effective vertical stress $\sigma_v$ can now be determined from FIG. 9 as both $\phi$ and $q_{max}$ are known.

After determination of $\sigma_v$, the plunger is slowly moved upwardly by operating piston A until the reading of load cell 18 is given by Equation 4.

$$LC_{18} = (\sigma_v + h\gamma_w)A_{pe} \qquad (4)$$

At this position, the pressure P, acting at the bottom of the plunger, is equal to the total vertical stress in the soil. Thus, the soil is unloaded from end bearing stress that resulted from the insertion of the apparatus. The pressure P and the upward movement $u_1$ needed to obtain P are recorded.

To eliminate any skin friction that might be acting on the friction sleeve, piston B is operated to slowly raise the friction sleeve until the readings of load cells 23 and 42 are equal.

DETERMINATION OF q-z CURVE

Figure 4A:
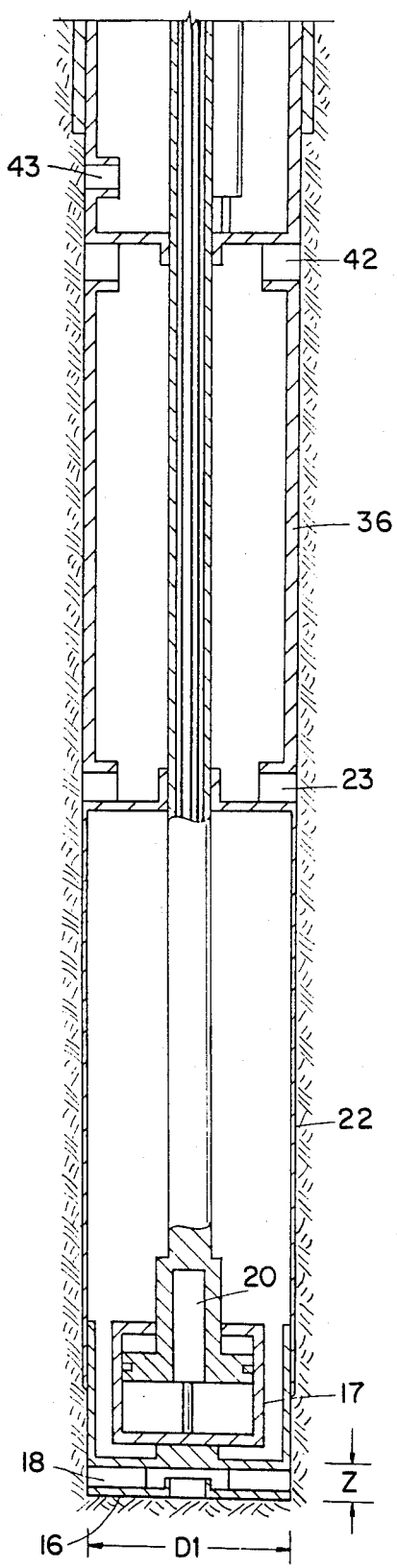
FIG. 4A is a vertical sectional view of the lower portion of the apparatus showing the position of the relatively movable elements of the apparatus after measurements have been made for determining the q-z curve.
Figure 4B:
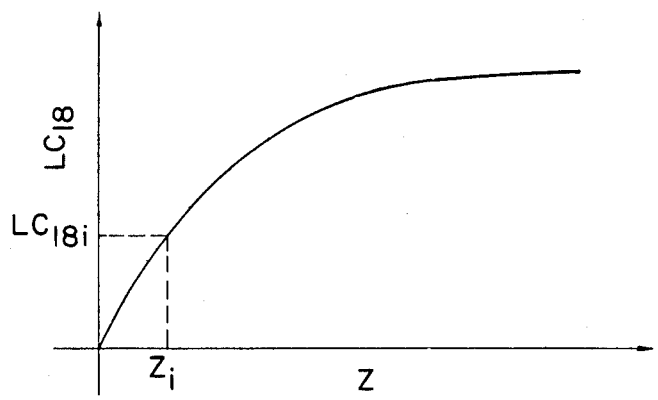
FIG. 4B is a representative curve plotted from the measurements obtained by the relative movement of the elements shown in FIG. 4A.

For this measurement the reading of load cell 18 is first adjusted to zero. Piston A is now slowly advanced to move the plunger a few inches into the soil (FIG. 4A). The soil resistance is measured by load cell 18, while the corresponding displacement, Z, is given by LVDT 20. These measurements are stored on magnetic tape and are recorded by the X-Y plotter at the surface. When plotted, the measurements produce a curve such as the curve shown in FIG. 4B.

For any particular movement $Z_i$, the mobilized unit end bearing, $q_i$, can be calculated as follows:

$$q_i = \frac{LC_{18i}}{A_{pe}} \qquad (5)$$

where, $LC_{18i}$ = the reading of load cell 18 corresponding to movement $Z_i$.

Using Eq. 5, the entire q-z curve can be generated.

DETERMINATION OF f-z CURVE (COMPRESSION)

After the measurements described above have been made to determine the q-z curve, piston A moves the plunger upwardly to unload the soil. The plunger should move by an amount equal to $u_l$. Prior to the measurement of skin friction, soil around the probe should consolidate. When pore pressure transducer 43 indicates the dissipation of most of the excess pore pressure that was generated during the insertion of the probe, the apparatus is ready for the next operation.

Figure 5A:
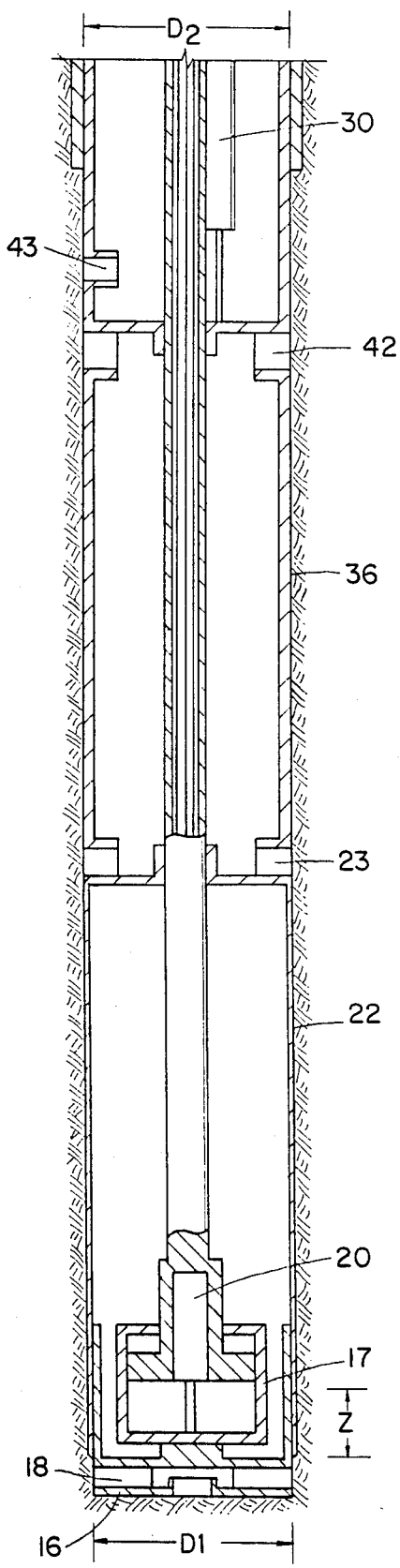
FIG. 5A shows the relative positions of the elements of the apparatus after making measurements of subsurface soil conditions for obtaining an f-z curve.
Figure 5B:
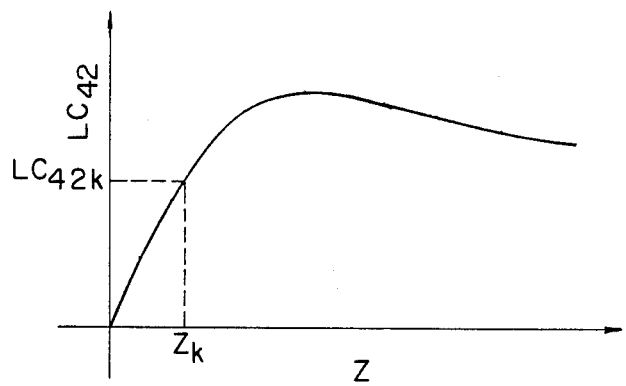
FIGS. 5B and 5C are representative curves plotted from the information obtained by the step shown in FIG. 5A.
Figure 5C:
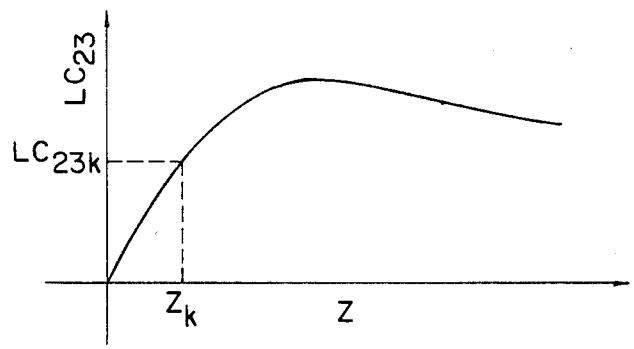

The readings of load cells 23 and 42 are adjusted to zero. The friction sleeve is now slowly pushed downwardly by piston B (FIG. 5A). The movement, z, of the friction sleeve, which is measured by LVDT 30, and the readings of load cells 23 and 42 during the movement are stored on magnetic tape and also recorded on the X-Y plotter. The measurements will follow curves like those shown in FIGS. 5B and 5C.

Mobilized, when used to qualify end bearing or skin friction, means the end bearing or skin friction resistance mobilized by the soil to resist movement through it.

For any particular movement $z_k$, the mobilized skin friction, $f_k$, is given by Eq. 6.

$$f_k = \frac{1}{\pi D_2 l_f}(LC_{42k} - LC_{23k}) \qquad (6)$$

where, $LC_{42k}$ and $LC_{23k}$ are the readings of load cells 42 and 23 corresponding to movement $z_k$.

Following Eq. 6 the entire f-z curve (compression) can now be generated. By using two axially spaced load cells, such as load cells 23 and 42, the skin friction acting on friction sleeve 36 can be accurately measured since the difference in the reading of the load cells results from skin friction only.

DETERMINATION OF f-z CURVE (TENSION)

To unload the soil after measurement of skin friction in compression, the friction sleeve is slowly moved upwardly until the readings of load cells 23 and 42 are equal. The soil around the probe is now allowed to consolidate until the reading of pore pressure transducer 43 equals free field pore water pressure at this level.

To measure tensile skin friction, the readings of load cells 23 and 42 are adjusted to zero. Piston B is slowly moved upwardly. The distance, z, that the friction sleeve is moved and the readings of load cells 23 and 42 during this movement are stored on magnetic tape and also recorded on the X-Y plotter. Using these measurements the f-z curve (tension) can be generated following Eq. 6.

Cohesive soil is nonlinearly viscoelastic. Modulus degradation of such material depends mainly on the rate of loading, number of cycles, and amplitude of strain. By controlling the flow of hydraulic oil in a cylinder, the rate of loading and the amplitude of strain can be varied as desired.

For cyclic testing the whole probe is pushed downwardly into undisturbed soil. The soil is unloaded of the stresses produced by this movement in the manner described above. To unload the soil below the plunger, it should be moved upwardly by an amount equal to u. To remove any skin friction acting on the friction sleeve, it is slowly moved upwardly until the readings of load cells 23 and 42 are equal. The soil around the probe is now allowed to consolidate and the readings of load cells 23 and 42 are adjusted to zero.

Figure 6A:
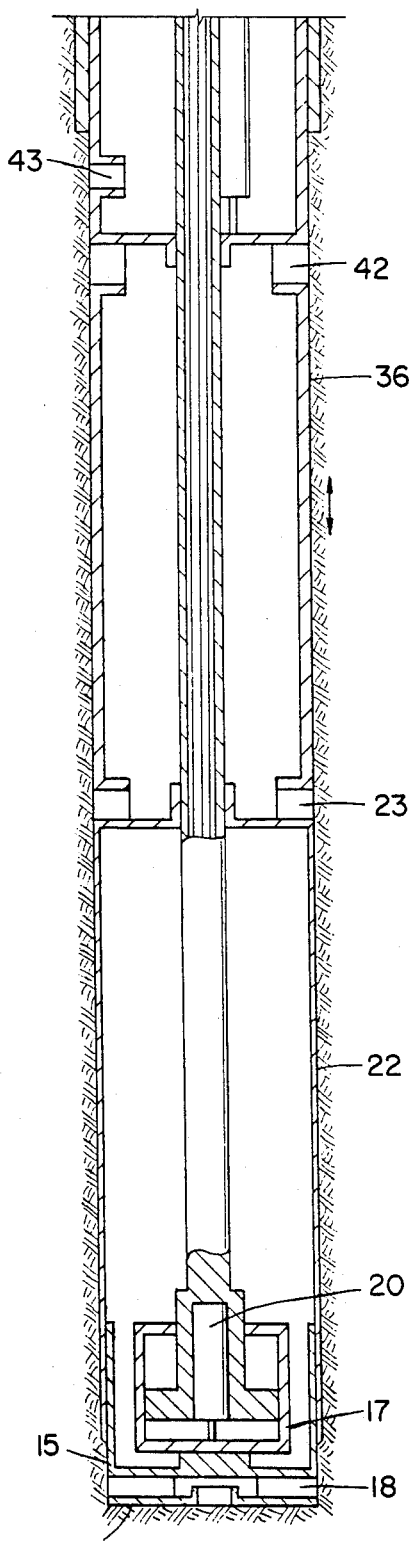
FIGS. 6A–6C show the manipulation of the apparatus and the curves of information obtained by cyclic loading of the soil by the apparatus of this invention.
Figure 6B:
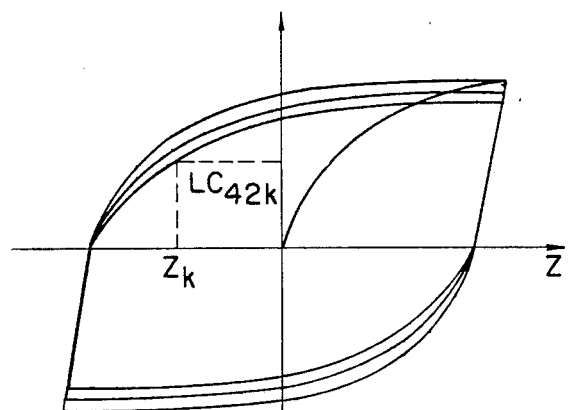
Figure 6C:
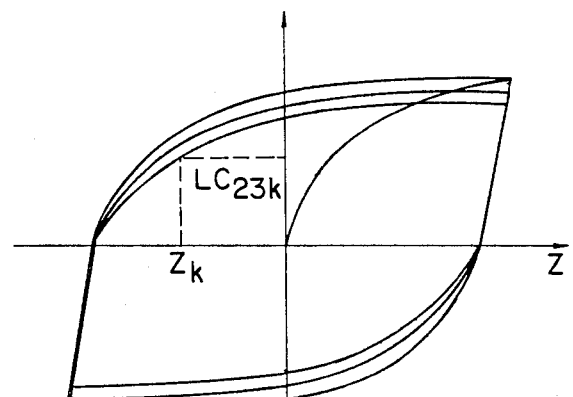

Piston B is now moved up and down a predetermined distance a predetermined number of times per unit of time to give a cyclic movement to the friction sleeve. The resistance versus movement curves for both downward and upward movements are recorded for each cycle so that the skin friction at the end of any desired number of cycles can be determined (FIGS. 6B and 6C). For each direction of movement and for any particular cycle, the variation of degraded skin friction with movement can be calculated following Eq. 6.

Granular soils are prone to liquefaction due to cyclic loading. To study the liquefaction potential of such soil around the probe, the friction sleeve is set in cyclic motion and the increase in pore pressure due to cyclic loading is monitored by pressure transducer 43.

After completion of all in situ tests, a soil sample is collected by sample tube 22, using piston B to push sample tube, 22, into the soil below plunger 15 the desired distance.

As stated above, the apparatus can be used without a borehole. In this case piston C and cylinder 50, with the latching device are not used and the flexible cable is run through a pushing rod. The surface electronics and other modules are housed inside a truck. A pushing mechanism from inside the truck pushes the rod. The weight of the truck is used as a counterweight.

The information obtained by the apparatus and method of this invention is directly applicable to the design of pile foundations. In addition, however, the following additional information can be obtained from the measurements it makes. This information can be used along with laboratory test results to gain more insight about the subsurface soil conditions.

Shear strength—The undrained shear strength of cohesive soil in situ, can be approximated from the relationship, $$S_u = \frac{q_{max}}{N_c}$$

where, $s_u$ = undrained shear strength;
$q_{max}$ = maximum unit end bearing;
$N_c$ = bearing capacity factor.

(ii) Overconsolidation ratio (OCR)—Correlation between $$\frac{S_u}{\sigma_v}$$

and OCR has been established and the information is available in the literature. Therefore, knowing the undrained shear strength, $S_u$ and the effective vertical stress, $\sigma_v$, the overconsolidation ratio can be approximated.

(iii) Stratigraphy—Reasonable stratigraphic correlations can be made from friction ratio data.

$$\text{Friction Ratio, } R_f(\%) = \frac{f_{a\,max}}{q_{max}} \times 100$$

In general, as the friction ratio increases soils grade from coarser to finer grained materials.

(iv) Angle of internal friction—The angle of internal friction, $\phi$, which is the most important parameter of granular soil, can be estimated from correlations between $\phi$ and $R_f$.

(v) Permeability—The dissipation of excess pore pressure in cohesive material as indicated by pressure transducer 43 provides qualitative information regarding permeability.

From the foregoing it will be seen that this invention is one well adapted to attain all of the ends and objects hereinabove set forth, together with other advantages that are obvious and that are inherent to the apparatus and method.

It will be understood that certain features and subcombinations are of utility and may be employed without reference to other features and subcombinations. This is contemplated by and is within the scope of the claims.

Because the invention may be embodied in other apparatus without departing from the scope thereof, it is to be understood that all matter herein set forth or shown in the accompanying drawings is to be interpreted as illustrative and not in a limiting sense.

The invention having been described, what is claimed is:

1. A method of determining the mobilized unit end bearing capacity of a soil in situ, comprising the steps of pushing a probe into the soil to the desired depth, said probe having a plunger for exerting a downward force on the soil, determining the effective vertical stress in the soil, raising the plunger until the pressure acting on the face of the plunger equals the total vertical stress in the soil to remove the stress created in the soil by the insertion of the plunger, measuring the net upward movement of the plunger, moving the plunger downwardly into the soil a preselected distance, measuring the force required to move the plunger said preselected distance to obtain a force vs distance curve for the plunger, and plotting mobilized unit end bearing of the soil against the distance the plunger is moved through the soil.

2. The method of claim 1 with the additional steps of moving a tubular member downwardly through the soil, plotting the force vs distance curve for the movement, and calculating the actual skin friction of the soil for compression.

3. The method of claim 1 with the additional steps of moving a tubular member upwardly through the soil, plotting the force vs distance curve for the movement, and calculating the actual skin friction of the soil for tension.

4. The method of claim 3 with the additional steps of moving the tubular member up and down at a predetermined rate through a predetermined distance and recording the forces opposing such movement as the tubular member moves through said distance to determine the degradation of the skin friction with cyclic motion.

5. Apparatus for obtaining values from which the actual bearing strength of a soil can be determined, comprising a tubular member, a plunger located in the lower end of the tubular member, means for moving the tubular member and the plunger relative to each other, means for measuring the force required to move each member separately, means for measuring the distance each member is moved, and means for measuring pore pressure at selected locations on said plunger and tubular member.

6. Apparatus for collecting information on sub-soil characteristics to determine the variations in resistance, q, at a pile tip due to tip movement, z, comprising means for simulating the tip of a pile, means for moving the tip simulating means into the soil to the desired level to measure the resistance of the soil a given movement of the tip simulating means from which the q-z curve for end bearing can be calculated, and means for raising the tip simulating means before making said measurement to unload the soil adjacent the tip simulating means from the bearing stresses imposed on the soil by the movement of the tip simulating means into the soil to the desired level.

7. Apparatus for measuring the skin friction of a soil comprising a probe of uniform diameter having an upper section and a lower section, a load cell located between the two sections to measure the forces exerted by the soil to movement of the lower section through the soil and a load cell located at the upper end of the upper section to measure the total force required to move the probe through the soil so that the difference in the readings of the load cells is the skin friction exerted by the soil to movement of the upper section through the soil.

8. The apparatus of claim 7 in which the lower section of the probe is an open-ended tubular member that will collect a sample of the soil when forced into the soil.

9. Apparatus for collecting information on sub-soil characteristics to determine the variations in resistance, q, at a pile tip due to tip movement, z, for measuring skin friction, and for obtaining a sample of the soil comprising means for simulating the tip of a pile, means for moving the tip simulating means into the soil to measure the resistance of the soil to movement of the tip simulating means from which the q-z curve for end bearing can be calculated, said apparatus further including a probe of uniform diameter having an upper section and a lower section, a load cell located between the two sections to measure the forces exerted by the soil to movement of the lower section through the soil and a load cell located at the upper end of the upper section to measure the total force required to move the probe through the soil so that the difference in the readings of the load cells is the skin friction exerted by the soil to movement of the upper section through the soil.

10. The apparatus of claim 9 in which the lower section of the probe is an open-ended tube that can be forced into the soil to obtain a sample of the soil.

* * * * *